United States Patent [19]

Küpper et al.

[11] Patent Number: 4,906,775
[45] Date of Patent: Mar. 6, 1990

[54] ESTERS OF 3-TERT-BUTYL- AND 3-TERT-BUTYL-5-ALKYL-4-HYDROXYPHENYL (ALKANE) CARBOXYLIC ACIDS WITH OXYETHYLATES OF POLYTHIOLS

[75] Inventors: Friedrich-Wilhelm Küpper, Marl; Heinz-Werner Voges, Dorsten; Hans-Jurgen Haage, Herne, all of Fed. Rep. of Germany

[73] Assignee: Huels Aktiengesellschaft, Marl, Fed. Rep. of Germany

[21] Appl. No.: 122,724

[22] Filed: Nov. 18, 1987

[30] Foreign Application Priority Data

Nov. 18, 1986 [DE] Fed. Rep. of Germany ....... 3639353

[51] Int. Cl.$^4$ .............................................. C07C 69/88
[52] U.S. Cl. .................................... 560/75; 8/DIG. 9
[58] Field of Search ....................... 560/75; 8/DIG. 9

[56] References Cited

U.S. PATENT DOCUMENTS 3,984,460 10/1976 Spivack ................................. 560/75
4,417,071 11/1983 Rosenberger ......................... 560/75

*Primary Examiner*—Paul J. Killos
*Attorney, Agent, or Firm*—Millen, White & Zelano

[57] ABSTRACT

Esters of 3-tert-butyl- and 3-tert-butyl-5-alkyl-4-hydroxyphenyl (alkane) carboxylic acids with oxyethylates of polythiols are useful as stabilizers for polymers, especially for polyethylene and polypropylene.

24 Claims, No Drawings

ESTERS OF 3-TERT-BUTYL- AND 3-TERT-BUTYL-5-ALKYL-4-HYDROXYPHENYL (ALKANE) CARBOXYLIC ACIDS WITH OXYETHYLATES OF POLYTHIOLS

CROSS-REFERENCE TO RELATED APPLICATION

This invention is related to coassignee's concurrently filed application, Ser. No. 122,722 entitled "Esters of 3-tert-butyl- and 3-tert-butyl-5-alkyl-4-hydroxyphenyl (alkane) Carboxylic Acids With Oxethylates of Polyhydroxyaromatics, Process for Their Production, and Their Use as Stabilizers", and and coassignee's concurrently filed application, Ser. No. 123,425 entitled "Esters of 3-tert-butyl or 3-tert-butyl-5-alkyl-4-hydroxyphenyl-(alkane) Carboxylic Acids with Oxethylates of Bis-(4 or 2-Hydroxyphenyl) Alkanes, Oxides, Sulfides and Sulfones, of Tris-(4-hydroxy-phenyl) Alkanes and of 1,3,5-tris-(4hydroxyphenylisopropylidene) Aryls".

BACKGROUND OF THE INVENTION

The present invention relates to esters of 3-tert-butyl- and 3-tert-butyl-5-alkyl-4-hydroxyphenyl (alkane) carboxylic acids, their preparation and their use as polymer stabilizers.

It is known that organic polymers as obtained by polymerization (or copolymerization) of mono- and diolefins, optionally containing functional groups, or by polycondensation of suitable precursors—for example, of diols with dicarboxylic acids—can suffer changes under the effect of air/oxygen, heat, light, or high-energy radiation; these changes impair the properties of the polymers important in their practical usage, such as strength, hardness and elongation. On account of such impairments, there is frequently not only a marked change in measurable physical properties, but also a visually noticeable softening, brittleness and/or discoloration of the finished articles also occur. For this reason, stabilizers are added to the corresponding polymers prior to processing. For more details, see the review publications by G. Scott, "Atmospheric Oxidation and Antioxidants", Elsevier Publ. Co., Amsterdam, Oxford, N.Y. (1965); R. Güchter, H. Müller, "Taschenbuch der Kunststoff-Additive" [Pocket Manual of Plastics Additives], C. Hanser Publishers, Munich/Vienna (1979); J. Pospisil in "Degradation and Stabilization of Polymers" (Edit.: H. Jellinek), Elsevier, Amsterdam, Oxford, N.Y. (1983), pp. 193 et seq.; P. P. K Lemchuk et al., "Polymer Degradation and Stabilization" 7:131 et seq. (1984).

It is also known that in case of polyolefins, compounds containing phenolic hydroxy groups are preferably utilized as stabilizers, and that, among these phenol derivatives, materials having voluminous alkyl groups, preferably with tert-butyl substituents, in at least one ortho position with respect to the phenolic hydroxy group, exhibit a particularly high efficacy. Esters can also be found among the large number of stabilizers disclosed (compare, for example, J. C. Johnson, "Antioxidants", Noyes Data Corp., 1975; M. W. Ramsey, "Antioxidants—Recent Developments", Noyes Data Corp., 1979; M. T. Gillies, "Stabilizers for Synthetic Resins", Noyes Data Corp., Park Ridge, N.J., 1983). Esters of 3,5-dialkyl-4-hydroxyphenyl(alkane) carboxylic acids are described for example in U.S. Pat. Nos. 3,681,431; 3,330,859; 3,644,482; 3,285,855; 4,598,113; esters of 4,6-dialkyl-3-hydroxyphenyl(alkane) carboxylic acids are disclosed in U.S. Pat. Nos. 3,988,363; 3,862,130; esters of 2-methyl-4-tert-butyl-5-hydroxyphenylalkane carboxylic acids are set forth in European Pat. No. 0,048,841.

The efficacy of the phenolic stabilizers can frequently be increased by adding specific compounds which in most cases contain sulfur or phosphorus. The optimum quantitative ratio of stabilizer and synergist is always to be found empirically in each individual instance.

The stabilizers as well as the synergists must meet the criteria that they can be incorporated without difficulties into the various polymers without decomposing, and that they can be distributed therein with maximum uniformity. On the other hand, the polymer should, at the required high incorporation temperatures, neither be discolored by additives nor suffer molecular degradation temperature load and shear stress.

In the literature, there are various stabilizer compounds disclosed which contain, besides sterically protected hydroxy phenyl groups, sulfur atoms which function synergistically in the same molecule (cf., e.g., R. W. Layer, "Non-staining Antioxidants" (in G. Scott, "Developments in Polymer Stabilization 4 (1981), p. 163 ff, p. 167); F. X. O'Shea in "Advances Chem. Series" 85 (1968), p. 128 ff; G. Scott in "Developments in Polym. Stabiliz." 6 (1983), p. 29 ff). In particular, derivatives of ortho-thiobisphenol are disclosed as strongly discoloring, and are probably used only for stabilizing rubber mixtures.

SUMMARY OF THE INVENTION

It is thus an object of this invention to provide improved stabilizers, their preparation and their use.

Upon further study of the specification and appended claims, further objects and advantages of this invention will become apparent to those skilled in the art.

To obtain these objects, there are provided novel esters of 3-tert-butyl or 3-tert-butyl-5-alkyl-4-hydroxyphenyl-(alkane) carboxylic acids of formula I

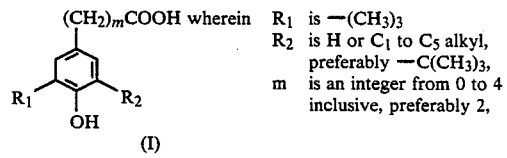

wherein $R_1$ is $-(CH_3)_3$
$R_2$ is H or $C_1$ to $C_5$ alkyl, preferably $-C(CH_3)_3$,
m is an integer from 0 to 4 inclusive, preferably 2, with oxethylates of polythiol aromatics of formulae II and III having 2 to 6 thiol groups and of dithiol-cycloalkanes of formula IV, said oxethylates containing a maximum of 6 alkylene oxide units, the preferred oxethylates being of the polythiols of formula II,

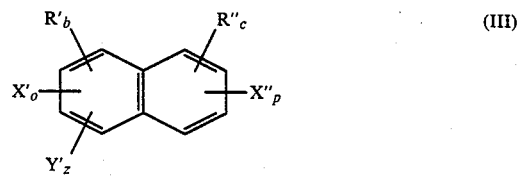

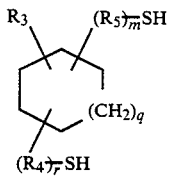

wherein
X represents $(CH_2)_mSH$
X' represents $(CH_2)_rSH$
X" represents $(CH_2)_2SH$ (in which each of m, r and s is 0 or 1),
R, R', R" represent H, alkyl, halogen, or hydroxyl,
$R_3$ represents H, $C_1$ to $C_4$ alkyl,
$R_4$, $R_5$ represents $C_2$ to $C_4$ alkylene,
q is an integer from 0 to 7, inclusive, being preferably 1, y represents 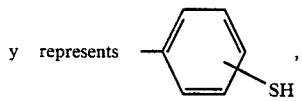, n is an integer from 2 to 6, inclusive, when z or z' represents 0,
n is an integer from 1 to 5, inclusive, when z or z' is other than 0,
O+p equals n
$0 \leq a$, $z \leq a+z \leq 6-n$ (in formula II)
$0 \leq b$, c, $z' \leq 4 \leq 8-(o+p)$ (in formula III)

Such esters are used as stabilizing agents of organic polymers, preferably polyolefins.

Thus, another object of the invention is, starting from 3-tert-butyl or 3-tert-butyl-5-alkyl-4-hydroxyphenyl-(alkane) carboxylic acids or their derivatives, preferably 3-(3,5-di-tert-butyl-4-hydroxyphenyl) propionic acid derivative(s), known in the art, by reaction with selected alcohols economicalto produce and containing sulfur as heteroatom to attain esters of these 3-tert-butyl or 3-tert-butyl-5-alkyl-4-hydroxyphenyl-(alkane) carboxylic acids of formula I with improved stabilizer properties, and by working these esters into organic polymers, preferably into polypropylene and polyethylene, to achieve a good stabilization of such polymers in regard to molecular weight degradation during processing or during use over a prolonged period, without any appreciable discoloration occurring as a result of the addition of stabilizer under such conditions.

Keys to the present invention are, as the alcohols, available or producible oxethylates of polythiol aromatics with 2 to 6 thiol groups of general formulae II and III, preferably of formula II, with 2 to 4 thiol groups, or of dithiolcycloaliphatics of formula IV, said oxethylates preferably having one alkylene oxide unit per thiol group.

Preferably esters are used, in which all thiol groups of the polythiol aromatics or dithiolcycloaliphatics are oxethylated each with one alkylene oxide of 2 to 8 carbon atoms, preferably ethylene oxide, and in which preferably all the thus resulting 2-hydroxy-(2-alkyl)-ethylthio ether groups are esterified. Esters of 3-(3,5-di-tert-butyl-4-hydroxyphenyl) propionic acid with poly-(monooxethylates), i.e., poly-(2-hydroxyethylthio ethers), of polythiol aromatics of formula II are especially preferred.

The stabilizing activity of the esters is exceptionally surprising. It could not be foreseen that with the esters according to the invention based on polythiol aromatics of formulae II and III or of cycloalkanedithiols of formula IV, stabilizers can be obtained, which contain at least two such thio ether bonds and yet which can be worked in, undecomposed, at the high temperatures of polyolefin processing. Furthermore, in addition to the high activity of the stabilizers, only a surprisingly slight discoloration of the resultant polymer materials is observed.

The properties of the stabilizers according to the invention, which contain aryl or cycloalkyl substituents in the sulfur-containing polyol component, are all the more surprising, since esters of 3,5-dialkyl-4-hydroxyphenyl-(alkane) carboxylic acids with monofunctional alkyl thio alcohols or thio alkane diols of the formulae $RS(CH_2)_nOH$ or $HO(CH_2)_mS(CH_2)_nOH$ (with m, n>1), being producible according to the prior art (cf U.S. Pat. No. 3,441,575, BE-PS No. 637 444), and some of them being commercially available, tend to discolor considerably. (See comparative example 37, infra.) On the other hand, liquids are mainly involved especially in the case of derivatives of alcohols with relatively short aliphatic chain ($R<C_8$) and containing only one sulfur atom.

The action of the esters according to the invention as stabilizers for polyolefins is also amazing, because according to the prior art some of polythiol aromatics of formula II with m=0 and z=0 are exceptionally strong reducing agents, which react immediately with oxygen and therefore are difficult to handle and are best handled under anaerobic conditions (cf., e.g., F. Wudl et al., J. Org. Chem. 50 (1985), 2395). Therefore, it was not easily to be expected that from such labile compounds by incorporation of alkylene oxide units, preferably of ethylene oxide, and esterification of the poly-(thio ether alcohols), that highly active stabilizers would become available, whose handling presents no problems whatsoever.

The esters to be used as stabilizers according to the invention, preferably for polypropylene and polyethylene, are novel, mainly crystalline compounds which are elucidated in the attached examples by melting points and spectroscopic studies.

The production of the esters according to the invention can take place according to processes known in the art by reaction of functional acid derivatives with polyfunctional alcohols available by oxethylation of said initial materials. These alcohols should contain at least two, preferably $\geq 2$, alkylene oxide units, i.e., exhibit at least two thio ether bridges, and these thio ether bridges proceed from at least two different thiol groups. For oxethylation, the known processes of the prior art (cf. e.g., M. J. Schick, "Nonionic Surfactants," Vol. I, M. Dekker, New York (1967), p. 175 ff; Houben-Weyl, "Methoden der organischen Chemie" [Methods of Organic Chemistry], Vol. VI/3 (1965), p. 461 ff) are used, according to which alkylene oxides of formula V

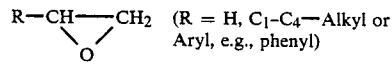 (R = H, $C_1$-$C_4$—Alkyl or Aryl, e.g., phenyl)

are added to the corresponding initial materials of formulae II to IV. Addition products of ethylene oxide, i.e., R=H in formula V, are preferred as starting materials for the esters of 3-tert-butyl or 3-tertbutyl-5-alkyl-4-hydroxyphenyl-(alkane) carboxylic acids of formula I according to the invention.

Ethylene oxide adducts of thiols can be obtained according to the prior art also by reaction of thiols with ethylene carbonate (cf., e.g., U.S. Pat. No. 2,448,767) or from suitable halogen-containing precursors by reaction with 2-thio ethanol ($HSCH_2CH_2OH$) by base catalysis according to

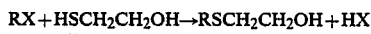

(cf. e.g., Ullmann, Enzyklopaedie der Techn. Chemie [Encyclopedia of Industrial Chemistry], Vol. 23 (1983), p. 186).

Very particularly preferred precrsors are poly-(monooxethkylates) of polythiol aromatics of dithiolcycloalkanes, in which all thiol groups by the action of ethylene oxide are converted into (2-hydroxyethylthio) substituents. Some poly-(2-hydroxyethylthio) aromatics or cycloalkanes corresponding to formulae II and IV, have already been described in J. Pharm Soc. Japan 75, 1560 (1955) (cf. CAS 1956, 10690 f); Beilstein, Vol. 6 III, 4610 a.

Separation of the desired poly-(monooxethylates) from by-products possibly arising during oxethylation, as, e.g., polyglycols or higher oxethylates, can be conducted according to known processes of the prior art, i.e., by crystallization from suitable solvents (such as alcohols or others), by column chromatography or—in individual cases—distillation under reduced pressure.

The production of esters according to the invention is especially simple, if the sulfur-containing poly(monooxethylates) are transesterified with esters of 3-tert-butyl or 3-tert-butyl-5-alkyl-4-hydroxyphenyl(alkane) carboxylic acids of formula I, preferably with esters of 3-(3,5-di-tert-butyl-4-hydroxyphenyl) propionic acid, which contain alkoxy groups with one to four C atoms, with release and removal of more readily volatile alcohols. The transesterification is generally performed at elevated temperature, e.g., about 100° to 150° C., preferably below 140° C. The direct reaktion of polyol and lower alkyl esters is often the most economical way, but it is also possible to operate in the presence of inert solvents or entraining agents for separation of the released alcohol. For acceleration of the transesterification, preferably basic or neutral catalysts according to the prior art are used, such as, e.g., sodium methylate, lithium amide, potassium tertbutylate, titanium tetrabutylate, aluminum triisopropylate. These are generally used in amounts of 0.1 to 5% by weight, in relation to the weight of the reaction mixture, and amounts of 0.5 to 1.5% by weight are preferred for reasons of reaction rate and cost.

The transesterification is suitably performed under inert gas or at reduced pressure, to avoid oxidation of the starting materials or the reaction products and to keep the reaction temperature relatively low, especially in the presence of the transesterification catalysts. It is advantageous to use one of the starting materials in 10 to 20% molar excess of the necessary stoichiometric amount. The reaction is interrupted as soon as most of, if not all of the stoichiometrically deficient component is consumed, as indicated by analysis of the reaction mixture or by weighing of the separated alcohol. For this purpose, the catalyst is inactivated (i.e., in the case of basic or neutal catalysts, e.g., is destroyed by addition of an equivalent amount of acid); the reaction mixture is worked up and the sulfur-containing polyol esters are purified by recrystallization from suitable solvents such as, e.g., alcohols, ethers or aromatic hydrocarbons. Then, the structure of the compounds is confirmed by $^1H$-NMR spectroscopy by means of the position and intensity of the different signals.

The 3-tert-butyl or 3-tert-butyl-5-alkyl-4-hydroxyphenyl-(alkane) carboxylic acid esters of poly-(2hydroxyethylthio) or poly-(2-hydroxyethylthiomethyl) aromatics as well as of di[2-hydroxyethyl thio-(alkyl)-]cycloalkanes according to the invention are valuable stabilizers for polymers, preferably for (co)polymers of monoolefins and/or diolefins, especially of polypropylene and plyethylene. Other suitable polymers e.g. are polybutadiene, Polyoctenamere and/or Polystyrene.

The stabilizers can be used as both processing stabilizers and as long-term stabilizers. The mixing in of the polymers can take place according to known processes of the prior art by mixing pulverulent polymers with the stabilizers or with a stabilizer concentrate (in the respective polymer). But the addition of stabilizer can also be made in a suspension, emulsion or solution of the polymers before working up. The stabilizers are used in amounts of about 0.02 to 3% by weight of the material to be stabilized, but the optimal amount, easy to determine by a polymer chemist man of the art, fluctuates as a function of each polymer to be stabilized and the type of processing or exposure.

An advantageous range is between 0.05 and 2% by weight of stabilizer addition, especially 0.1 to 1% by weight in the case of polyolefins. In any case, the stabilizer can comprise one or more individual esters. Furthermore, other additives such as, e.g., organic compounds containing sulfur and/or phosphorus as synergists as well as different (not according to the invention), plasticizers, pigments, UV stabilizers, antistatic agents, fillers and/or processing auxiliary agents, such as calcium stearate, can also be incorporated and worked into the polymers.

The resultant stabilized polymers according to the invention, especially polyolefins, can be processed by the injection-molding or extrusion process into finished products that can be used for many fields of application.

Without being bond by the meohanism of the invention, it is believed that the stabilizers are useful for a broad variety of polymers.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1 (NOT ACCORDING TO THE INVENTION)

Production of 1,4-bis-(2'-hydroxyethytlthiomethyl) benzene 0.85 mol (19.54 g) of sodium is first dissolved under inert gas in 400 ml of absolute ethanol in a carefully dried apparatus of a 1,000-ml three-neck flask with reflux condenser, stirrer, dropping funnel with presure compensation and inert gas inlet connection. Then 0.85 ml (66.4 g) of thioethnol is added and 0.4 mol (70 g) of 1,4-bis-(chloromethyl) benzene, dissolved in 200 ml of ethanol, is instilled within about 10 minutes to the thus resulting sodium (2-hydroxyethyl mercaptide) with stirring at 20° C. After about a 5-hour second reaction time at boiling temperature of the reaction mixture, the precipitating sodium chloride is filtered off after cooling of the solution to room temperature. 1,4-bis(2'-hydroxyethyl thiomethyl) benzene in the form of colorless crystals crystallizes out of the filtrate after drawing off of a part of the solvent.

Yield: 81.2 g (=78% of theory)
Melting point: 91° C. (from ethanol).

The constitution of the compound is verified by the position and intensity of the signals of the $^1$H NMR spectrum.

EXAMPLE 2

Production of di-[3-(3,5-di-tert-butyl-4-hydroxyphenyl) propionic acid] ester of 1,4-bis-(2'-hydroxyethylthiomethyl) benzene 0.29 mol (75 g) of 1,4-bis-(2'-hydroxyethylthiomethyl) benzene is mixed with 0.62 mol (181.3 g) of 3-(3,5-di-tertbutyl-4-hydroxyphenyl) propionic acid methyl ester and 0.076 mol (4.1 g) of sodium methylate in a three-neck flask equipped with an internal thermometer, magnetic stirrer and Liebig condenser. The reaction mixture is heated to 110° C. to 115° C. in an apparatus dried before the reaction with exclusion of moisture and under inert gas. After about one hour of reaction time the pressure is reduced step by step to about 0.2 hPa (mbar). The methanol to be distilled off is condensed in a cold trap and weighed for appraisal of the reaction achieved after conclusion of the transesterification. Virtually complete reaction is achieved after about 8 hours. After cooling of the reaction mixture with exclusion of air the content of the three-neck flask is taken up in about 250 to 300 ml of toluene, a nearly equivalent amount of glacial acetic acid (5% excess) is added to the sodium methylate catalyst and the toluene solution is then washed with sodium bicarbonate solution and water. After filtration and drying the toluene is first removed at reduced pressure, before the unreacted or excessive 3-(3,5-di-tert-butyl-4-hydroxyphenyl) propionic acid methyl ester (bp about 130° C./0.05 hPa (mbar)) is separated in a vacuum from the viscous distillation residue. The nonvolatile portions of the reaction mixture consist mainly of the bis-(3-(3,5-di-tert-butyl-4-hydroxyphenyl) propionic acid) ester of 1,4-bis(2'hydroxyethylthiomethyl) benzene. By addition of a small amount (about 180 ml) of diethyl ether the diester can be brought to crystallization. The raw product is purified by recrystallization from diethyl ether up to melting point constancy, the purity achieved is rechecked by thin-layer chromatography (TLC).

Yield: 160 g (=70.9% of theory)
Melting point: 95.5° to 96.5° C.
purity: 92% (according to TLC)

The constitution of the compound is verified by the intensity and position of the signals of the $^1$H NMR spectrum. (Cf. table I, which contains greater details on the spectra of the esters according to the invention (taken up with TMS (tetramethylsilane) as the internal standard mainly in CDCl$_3$).

EXAMPLE 2.1

Example 2 is repeated with the use of 0.15 mol (38.8 g) of 1,4-bis-(Z-hydroxyethylthiomethyl) benzene, 0.33 mol (96.5g) of 3-(3,5-di-tert-butyl-4-hydroxyphenyl) propionic acid methyl ester and 0.01 mol (3.4 g) of titanium tetrabutylate (instead of sodium methylate). After 6 hours an almost complete reaction of the diol used is achieved. After working up, the bis-(3-(3,5-di-tert-butyl-4-hydroxyphenyl) propionic acid) ester of 1,4-bis-(2'hydroxyethylthiomethyl) benzene is obtained in 75.1% (87.8 g) yield.

Melting point: 96° to 96.5° C. (from diethyl ether)
Purity: ≧95% (according to $^1$H NMR)

EXAMPLES 3 TO 9 (not according to the invention)

Production of different poly-(2-hydroxyethylthiomethyl) benzene compounds

According to the procedure described in Example 1, 0.5 to 2.0 mol of sodium-(2-hydroxyethyl mercaptide) is reacted with 1,2-bis-(chloromethyl) benzene (Example 3), 1,4-bis(bromomethyl)2,3,5,6 tetrabromobenzene (Example 4), 1,3,5-trichloro-2,4,6-tris-(bromomethyl) benzene (Example 5), 1,4-dichloro-2,3,5,6-tetra-(bromomethyl) benzene (Example 6), 1,4-dibromo-2,3,5,6-tetra-(bromomethyl) benzene (Example 7), methyl-penta-(bromomethyl) benzene (Example 8) and hexa(bromomethyl) benzene (Example 9) to the corresponding poly(2-hydroxethylthiomethyl) benzene compounds. In all cases a slight excess (about 5 mol %) of sodium-(2-hydroxyethyl mercapcide) is used. In the case of haloqenmethyI aromatics of low solubility in ethanol the reaction is to be performed in dry diethylone glycol dimethyl ether, and the second reaction time after mixing of the initial materials is optionally to be extended to achieve complete exchange of all halogen atoms. Precipitating sodium halide is filtered off and the poly-(2-hydroxyethylthiomethyl) aromatics are isolated after concentration of the filtrates by evaporation. For further purification the polyols are to be recrystallized until products with constant melting points are abtained whose constitution is rechecked by means of $^1$H NMR analysis. Table II contains a compilation of synthesized, largely previously undescribed compounds with the solvents used for the production or recrystallization as well as with the determined melting points and yields.

EXAMPLE 10

Production of bis-(3-(3,5-di-tert-butyl-4-hydroxyphenyl) propionic acid) ester of 1,2-bis-(2'hydroxyethylthiomethyl) benzene According to the procedure described in Example 2, 0.27 mol (69.7 g) of 1,2-bis-(2'hydroxyethylthiomethyl) benzene (melting point 10° C.), which was produced according to Example 3, is transesterified in the presence of 0.15 mol (8.26 g) of sodium methylate with 0.57 mol (166.7 g) of 3-(3,5-di-tert-butyl- 4-hydroxyphenyl) propionic acid methyl ester at 115° C. within 5.5 hours. After working up and removal of untransesterified or excess initial materials under reduced pressure, a viscous oil is obtained, which after prolonged cooling (also with addition of slight amounts of solvents) does not crystallize. The $^1$H NMR spectrum verifies the constitution of the diester. Purity: >95% (according to 1H NMR).

EXAMPLE 11

Production of bis-(3-(3,5-di-tert-butyl-4-hydroxyphenyl) propionic acid ester of 1,4-bis-(2'hydroxyethylthiomethyl) 2,3,5,6-tetrabromobenzene According to the procedure described in Example 2, 0.13 mol (74.6 g) of 1,4-bis-(2'hydroxyethylthiomethyl) 2,3,5,6-tetrabromobenzene (melting point 170° to 171° C.), which was produced according to Example 4, is transesterified with 0.31 mol (90.7 g) of 3-(3,5-di-tert-butyl-4-hydroxyphenyl) propionic acid methyl ester in the presence of 0.005 mol (1.7 g) of titanium tetrabutylate, which was used as catalyst instead of sodium methylate, at 145° C. within 7.6 hours. Similar working up yields a raw product, from which the bis-ester according to the invention is obtained after recrystallization from ethanol.

Yield: 126.5 g of bis-ester (=88.5% of theory)
Melting point: 109.5° C. (from ethanol)
Purity: >95% (according to TLC)

The constitution of the compound is verified by the position and intensity of the signals of the $^1$H NMR spectrum. (For details, cf. Table I).

EXAMPLE 12

Production of tris-(3-(3,5-di-tert-butyl-4-hydroxyphenyl) propionic acid ester of 1,3,5-tris-(2'hydroxyethylthiomethyl)-2,4,6-trichlorobenzene 0.08 mol (35 g) of 1,3,5-tris-(2'hydroxyethylthiomethyl)-2,4,6-trichlorobenzene (melting point 140° C. to 141.5° C.) obtained according to Example 5 is transesterified according to the procedure described in Example 2 in the presence of 0.005 mol (1.7 g) of titanium tetrabutylate with 0.24 mol (70.9 g) of 3-(3,5-di-tert-butyl-4-hydroxyphenyl) propionic acid methyl ester at 135° C. within 5.5 hours with removal of the methanol being freed at reduced pressure. After similar working up and removal of unreacted or excessive initial materials, a viscous residue is obtained, which hardens like glass when cooled. It consists of the tris-ester according to the invention. Its constitution is verified by the position and intensity of the signals of the $^1$H NMR spectrum. (Cf. Table I).

Yield: 71 g (=74.3% of theory) tris-ester
Melting point: 56° C. to 61° C.
Purity: ≧95% (according to $^1$H NMR)

EXAMPLE 13

Production of tetra-(3-(3,5-di-tert-butyl-4-hydroxyphenyl) propionic acid) ester of 1,2,4,5-tetra-(2'-hydroxyethylthiomethyl)-3,6-dichlorobenzene According to the procedure described in Example 2, 0.14 mol (53.2 g) of 1,2,4,5-tetra-(2'-hydroxyethylthiomethyl)-3,6dichlorobenzene (melting point 165° to 170.° C.), which was produced according to Example 6, is transesterified with 0.61 mol (177.2 g) of 3-(3,5-di-tert-butyl-4-hydroxyphenyl) propionic acid methyl ester in the presence of 0.02 mol (6.4 g) of titanium tetrabutylate at 135° to 140° C. within 26 hours. After working up and removal of unreacted or excessive initial materials under reduced pressure, the tetra ester of the tetrafunctional alcohol containing sulfur is obtained. Its constitution is verified by the $^1$H NMR spectrum. (More details are to be found in table I.)

Yield: 162.4 g (=78.3% of theory) tetra-ester
Melting point: 133° to 136° C. (from ethanol)
Purity: 95% (according to $^1$H NMR)

EXAMPLE 14

Production of tetra-(3-(3,5-di-tert-butyl-4-hydroxyphenyl) propionic acid) ester of 1,2,4,5-tetra-(2-hydroxyethylthiomethyl)-3,6-dibromobenzene Analogously to Example 2, 0.12 mol (71.6 g) of 1,2,4,5-tetra-(2'hydroxyethylthiomethyl)-3,6-dibromobenzene (melting point 172.5° to 174° C.), which was obtained according to Example 7, is transesterified in the presence of 0.011 mol (3.8 g) of titanium tetrabutylate with 0.52 mol (152.1 g) of 3-(3,5-di-tert-butyl-4-hydroxyphenyl) propionic acid methyl ester within 22 hours at 135° C. After similar working up and removal of unreacted or excessive initial materials, the tetra ester according to the invention remains, which is recrystallized from dioxane. Its constitution is established by $^1$H NMR spectrometry (cf. Table I).

Yield: 196.6 g (=75.5% of theory) tetra-ester
Melting point: 140° C. to 142° C. (from dioxane)
Purity: >95% (according to $^1$H NMR)

EXAMPLE 15

Production penta-(3-(3,5-di-tert-butyl-4-hydroxyphenyl) propionic acid) ester of penta-(2'-hydroxyethylthiomethyl) methyl benzene According to the procedure described in Example 2, 0.06 mol (34 g) of penta-(2'-hydroxyethylthiomethyl) methyl benzene (melting point 127° to 129° C.), which was produced according to Example 8, is transesterified in the presence of 0.005 mol (1.7 g) of titanium tetrabutylate with 0.35 mol (100.9 g) of 3-(3,5-di-tert-butyl-4-hydroxyphenyl) propionic acid methyl ester at 150° C. within 5.5 hours. After similar working up and removal of unreacted or excessive initial materials, a viscous residue is obtained, which solidifies like glass when it cools and consists of the penta ester according to the invention. Its constitution is verified by the $^1$H NMR spectrum. (Cf. Table I for more details).

Yield: 115.5 g (=78.2% of theory) penta-ester
Melting point: 55° to 56.5° C.
Purity: >95% (according to $^1$H NMR)

EXAMPLE 16

Production of hexa-(3-(3,5-di-tert-butyl-4-hydroxyphenyl) propionic acid) ester of hexa-(2-hydroxyethylthiomethyl) benzene According to the procedure described in Example 2, 0.028 mol (17.3 g) of hexa-(2-hydroxyethylthiomethyl) benzene (melting point 125° to 126.5° C.), which was obtained according to Example 9, is transesterified with 0.18 mol (51.6 g) of 3-(3,5-di-tert-butyl-4-hydroxyphenyl) propionic acid methyl ester within 8 hours at 134° C. in the presence of 0.016 mol (0.9 g) of sodium methylate. After similar working up and removal of unreacted or excessive initial materials, the hexa ester according to the invention is isolated. The $^1$H NMR spectrum verifies its constitution (cf. Table I).

Yield: 16.2 g (=26.5 of theory) hexa-ester

Melting point: 89.5° to 91.5° C. (from methanol)
Purity: about 93% (according to TLC) cl EXAMPLE 17 (not according to the invention)

Production of bis-2,9-(2'-hydroxyethylthio) para-menthane

According to known processes for oxethylation of mercaptans (cf., e.g., M. J. Schick, loc. cit.), dipentenedimercaptan (2,9-para-menthanedithiol) is reacted in the presence of catalytic amounts of sodium hydroxide with ethylene oxide. The reaction is stopped as soon as the amount of ethylene oxide corresponding to the two thiol groups is taken up. After cooling, neutralizing of the catalyst used with an equivalent amount of glacial acetic acid, removal of the sodium acetate formed and drawing off of the more readily volatile components at a pressure of less than 0.1 hPa (mbar), a viscous oil remains, from which the desired sulfur-containing diol can be separated by fractional distillation (boiling point 188° C./0.1 hPa (mbar). The $^1$H NMR spectrum verifies the constitution of the compound.

EXAMPLE 18

Production of bis-(3-(3,5-di-tert-butyl-4-hydroxyphenyl) propionic acid) ester of bis-2,9-(2'-hydroxyethylthio) paramenthane According to the procedure described in Example 2, 0.31 mol (90.7 g) of dipentenedimercaptan-bis-(monooxethylate) [bis-2,9-((2'-hydroxyethylthio) menthane], which was produced according to Example 17, is transesterified with 0.67 mol (196 g) of 3-(3,5-di-tert-butyl-4-hydroxyphenyl) propionic acid methyl ester in the presence of 0.01 mol (3.4 g) of titanium tetrabutylate at 120° C. within 16 hours, and methanol that becomes free is removed at reduced pressure. After similar working up as in Example 2 and removal of unreacted or excessive initial materials (at 0.03 hPa (mbar)),the diester according to the invention remains as a yellowish oil, which cannot be recrystallized either by prolonged cooling or by addition of small amounts of different solvents. The constitution of the diester is verified by the $^1$H NMR spectrum. (Further details can be gathered from Table I). Obviously the crystallization retardation is to be attributed to the presence of a mixture of conformers, since the purity of the bisester according to the $^1$H NMR spectrum should be >90%.

EXAMPLE 19 to 28

(Examples 26 to 28 are not according to the invention)
Stabilization of polypropylene with stabilizers according to the invention (Examples 19 to 25) and with stabilizers according to the prior art 2 kg of polypropylene powder is mixed with amounts indicated in Table II of stabilizer (esters according to the invention according to Examples 2 as well as 11 to 16 or stabilizers according to the prior art (in comparison Examples 26 to 28), of calcium stearate (0.1% by weight) as processing auxiliary agent as well as optionally of bis(octadecyl) thiodipropionic acid ester and of tris-(2,4-di-butylphenyl) phosphite and is mixed in a mixing unit (e.g., fluid mixer of Papenmeier company) at room temperature. The powder mixtures obtained are extruded at 100 rpm and a maximum of 230° C. with an extruder (Troester company, d=30 mm, 1=20 d) and then granulated. The granulate is molded at 210° C. to 1-mm thick plates and from them, polyolefin strips with measurements of 1×10×100 mm are punched.

The latter are stored in a suitable device at 145° C. free-standing in a forced-air drying cabinet in the presence of air until, as a sign of the starting embrittlement a crumbling of the test pieces or formation of cracks on them, can be observed. Table III contains the results.

From the resistance of the stabilized polypropylene test pieces determined at 145° C. it is recognized that the action of the esters to be worked in according to the invention reaches or exceeds generally the level of the test pieces in which stabilizers according to the prior art were added.

EXAMPLES 29 to 38

(Examples 36 to 38 are not according to the invention)
Examination of stabilized polyethylene test pieces for color changes Analogously to Examples 19 to 28, polyethylene granulates with 0.1% by weight of various stabilizers and always with 0.1% by weight of calcium stearate were molded at 210° C. into plates (with measurements of 4×10×100 mm). If these are subjected to a 28-day aging at 100° C. and then the different test pieces are assessed with respect to color changes that have occurred, in comparison with test pieces analogously produced and aged, which contain stabilizers according to the prior art [(mono-, bis- or tetra-(3-(3,5-di-tert-butyl-4-hydroxyphenyl) propionic acid) ester of octadecanol (Example 36), thiodiethanol (Example 37) or pentaerythritol (Example 38)], thus the visually determined color impressions reproduced in column 5 of Table III are obtained.

It is recognized from the test results that with the stabilization according to the invention advantages are to be achieved in comparison with the prior art, as it is represented by Example 37 for sulfur-containing stabilizers, since in Examples 29 to 35 without exception markedly slighter discolorations are observed, so that even the value level prescribed according to the prior art by sulfur-free stabilizers is almost reached.

EXAMPLES 39 to 48

(Examples 46 to 48 not according to the invention)

Stabilized, polypropylene powder produced according to Examples 19 to 25 as well as 26 and 28 was repeatedly extruded at a maximum of 270° C. on an extrusimeter (Goepfert company; d=20 mm, 1=20 d; 30 rpm). $I_5$ values as measurements for changes of the molecular weight were determined on the obtained granulates at 190° C. The determined values are summarized in Table IV.

It is recognized from the determined values that with the stabilizers according to the invention already without addition of synergists often a better, but at least as good a processing stability can be attained as with stabilizers according to the prior art. In the presence of additional synergists the differences from the prior art are smaller.

EXAMPLE 49

Production of 3-(3,5-di-tert-butyl-4-hydroxyphenyl) propionic acid esters of 1,4-dihydroxy-2,3,5,6-(tetra-(2'-hydroxyethylthio) benzene According to the procedure described in Example 2, 0.07 mol (b 29 g) of 1,4-dihyrdoxy-2,3,5,6-tetra-(2'-hydroxyethylthio) benzene, which (according to M.

Kulka, Can. J. Chem. 40 (1962) 1238) is accessible by reaction of chloranil with thioethanol, is transestserified in the presence of 0.34 mol (18.4 g) of sodium methylatea with 0.38 mol (111.1 g) of 3-(3,5,-di-tert-butyl-4-hydroxyphenyl) propionic acid methyl ester at 120° C. within 6 hours. After similar working up and removal of unreacted or excessive initial materials, a residue hardening on cooling is obtained, from which impurities of lower solubility are separated by repeated recrystallization from toluene. The solid residue remaining after drawing off of the toluene consists of a mixture of different 3-(3,5-di-tert-butyl-4-hydroxyphenyl) propionic acid esters of 1,4-dihydroxy-2,3,5,6-tetra-(2'hydroxyethylthio)benzene, in which the tetra ester predominates. The $^1$H NMR spectrum (measured in CDCl$_3$ against TMS (internally)) verifies the presumed constitution on the basis of the position of the resonance signals (at 7.0 to 7.2 ppm; 5.1 ppm, 4.15 to 4.3 ppm; 3.0 to 3.5 ppm; 2.5 to 2.7 ppm; 2.3 ppm and 1.43 ppm.).

TABLE I $^1$H NMR spectra of 3-(3,5-di-tert-butyl-4-hydroxyphenyl) propionic acid esters of oxethylates of different polythiol aromatics and dithiocycloalkanes

| Ester (alcohol) according to example No. | Resonance line of the $^1$H NMR spectra [in ppm]* (Classification according to structure formulas*** of esters according to the invention) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 2 (1) | 6,98 | 5,07 | 4,20 | 2,63 | 2,87 | 2,63 | 1,42 | 7,26 | 3,72 | | | |
| | (4) | (2) | (4) | (4) | (4) | (4) | (36) | (4) | (4) | | | |
| 10 (3) | 6,99 | 5,08 | 4,21 | 2,64 | 2,88 | 2,64 | 1,43 | 7,23 | 3,92 | | | 7,18 |
| | (4) | (2) | (4) | (4) | (4) | (4) | (36) | (2) | (4) | | | (2) |
| 11 (4) | 6,98 | 5,07 | 4,36 | 2,88 | | 2,62 | 1,43 | | 4,31 | | | |
| | (4) | (2) | (4) | (8) | | (4) | (36) | | (4) | | | |
| 12 (5) | 6,98 | 5,08 | 4,28 | 2,83 | | 2,63 | 1,42 | | 4,10 | | | |
| | (6) | (3) | (6) | (12) | | (6) | (54) | | (6) | | | |
| 13 (6)** | 6,90 | 6,70 | 4,23 | 2,86 | 2,75 | 2,57 | 1,33 | | 4,08 | | | |
| | (8) | (4) | (8) | (8) | (8) | (8) | (72) | | (8) | | | |
| 14 (7) | 6,98 | 5,13 | 4,33 | 2,88 | | 2,63 | 1,42 | | 4,26 | | | |
| | (8) | (8) | (8) | (12) | | (8) | (72) | | (8) | | | |
| 15 (8) | 6,98 | 5,07 | 4,37 | 2,90 | | 2,65 | 1,42 | | 4,13 | 3,95 | 2,47 | |
| | (10) | (5) | (10) | (20) | | (10) | (90) | | (6) | (4) | (3) | |
| 16 (9) | 6,98 | 5,05 | 4,37 | 2,87 | | 2,63 | 1,40 | | 4,12 | | | |
| | (12) | (6) | (12) | (24) | | (12) | (108) | | (12) | | | |
| 18 (17) | 6,98 | 5,10 | 4,20 | 2,68/2,86 | | 2,61 | 1,43 | | 2,98 | 2,39 | 0,8–2,1 | |
| | (4) | (2) | (4) | (6) | | (4) | | | (1) | (1) | | |

Explanations of Table I

*measured in CDCl$_3$ against TMS (internally), conc. about 20% by volume; there are indicated the signal positions in ppm (with TMS = 0 ppm) and the number of pertinent H atoms (in each case in parentheses)

**measured in d-DMSO (deutero-dimethyl sulfoxide)

***Classification of signals

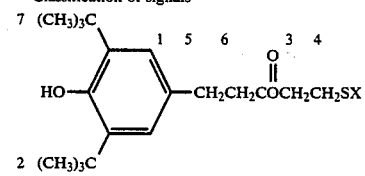

with X =

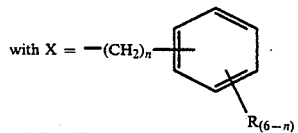

and R = H    8    12

—(CH$_2$)—    9

(for R = Cl, Br)

—(CH$_2$)—    9   10

(for R = CH$_3$    11 )

or with X =

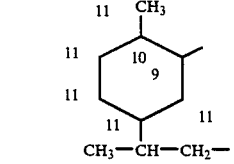

TABLE II

Sulfur-containing polyols used for the production of esters according to the invention
(cf. examples 3 to 9 and 17 not according to the invention)

| Polyol acc. to ex. Nr. | Formula of polyol (with X = SCH₂CH₂OH) | Initial product in polyol synthesis | Production of Polyols | | | |
|---|---|---|---|---|---|---|
| | | | Yield (% of th.) | Melt. point (°C.) | Solvent for recrystallization | Solvent during production |
| 1 | XCH₂—⟨C₆H₄⟩—CH₂X | X = Cl | 84.5 | 90–91.5 | Ethanol | Ethanol |
| 3 | ortho-C₆H₄(CH₂X)₂ | X = Cl | 66.2 | 10° | | " |
| 4 | Br₃C₆(CH₂X)₂ (tribromo with 2 CH₂X) | X = Br | 77.0 | 176–177 | Diglyme | " |
| 5 | Cl₃C₆(CH₂X)₃ | X = Br | 63.3 | 140–141.5 | Ethanol | Ethanol/Diglyme |
| 6 | Cl₂C₆(CH₂X)₄ | X = Br | 90.4 | 176–177 | Diglyme | Ethanol |
| 7 | Br₂C₆(CH₂X)₄ | X = Br | 81.0 | 179–180 | Diglyme | Ethanol |
| 8 | CH₃—C₆(CH₂X)₅ | X = Br | 62.3 | 127–129 | Ethanol | " |
| 9 | C₆(CH₂X)₆ | X = Br | 31.2 | 125–126.5 | Ethanol | Ethanol |
| 17 | CH₃-cyclohexyl with X and CH₃—CHCH₂X substituents | X = SH | | liquid (bp 188°/0.1) | | |

TABLE III

Aging tests at 145° C. or 100° C. with addition of stabilizers according to the invention for polypropylene or polyethylene

| Example No. | Stabilizer ac. to ex. No. | Formula of Stabilizer | Aging at 145° C. (days) A* | B* | C* | Color assessment (ex. 29–38) |
|---|---|---|---|---|---|---|
| 19(29) | 2 | X—⌬—CH$_2$SCH$_2$CH$_2$OCCH$_2$CH$_2$—⌬—OH with C(CH$_3$)$_3$ groups (FIG. X) | 22 | 38 | 40 | 0 |
| 20(30) | 11 | Tetrabromo-bis(X)-benzene | 27 | 48 | 52 | 0 |
| 21(31) | 12 | Trichloro-tris(X)-benzene | 48 | 73 | >84 | 0 |
| 22(32) | 13 | Dichloro-tetrakis(X)-benzene | 29 | 63 | 70 | 0 |
| 23(33) | 14 | Dibromo-tetrakis(X)-benzene | 26 | 65 | 62 | 0 |
| 24(34) | 15 | CH$_3$-pentakis(X)-benzene | 23 | 51 | 50 | 0 |
| 25(35) | 16 | Hexakis(X)-benzene | 11 | 31 | 33 | 0 |
| 26(36) | Vergleichsversuch nach dem Stand der Technik | CH$_3$(CH$_2$)$_{17}$OCCH$_2$CH$_2$—⌬—OH with C(CH$_3$)$_3$ groups (FIG. Y) | 3 | 10 | 13 | 0 |
| 27(37) | Vergleichsversuch nach dem Stand der Technik | Y—OCH$_2$CH$_2$SCH$_2$CH$_2$O—Y | 15 | 24 | 32 | — |
| 28(38) | Vergleichsversuch nach dem | C(CH$_2$O—Y)$_4$ | 50 | 74 | 81 | 0 |

TABLE III-continued

Aging tests at 145° C. or 100° C. with addition of stabilizers according to the invention for polypropylene or polyethylene

| Example No. | Stabilizer ac. to ex. No. | Formula of Stabilizer | Aging at 145° C. (days) A* | B* | C* | Color assessment (ex. 29-38) |
|---|---|---|---|---|---|---|
| | Stand der Technik | | | | | |

Explanations to Table II;
*Abbreviations:
A = 0.1% by weight of addition of stabilizer to polypropylene
B = as A and additionally 0.1% by weight of bis-(octadecyl) thiodipropionic acid ester
C = as B and additionally 0.1% by weight of tris-(2,4-di-tert-butylphenyl) phosphite
**Assessment of coloring of stabilized polyethylene test pieces at 100° C. after 4-weeks aging. (The data are always in relation to the comparison test (example 38).)
0: as good as example 38
(-): somewhat poorer than example 38
-: poorer than example 38
--: considerably poorer than example 38

TABLE IV

Multiple extrusion of stabilized polypropylene test pieces

| | Polypropylene | MFI Values (g/10 min) after multiple extrusion | | | | | | | | | | |
|---|---|---|---|---|---|---|---|---|---|---|---|---|
| Ex. | ac. to | Without addition of synergists* | | | | | | With addition of synergists** | | | | |
| No. | ex. No. | 0× | 1× | 2× | 3× | 4× | 5× | 0× | 1× | 2× | 3× | 4× | 5× |
| 39 | 19 | 3.0 | 4.6 | 7.3 | 11.9 | 13.5 | 17.5 | | | | | |
| 40 | 20 | 3.4 | 7.4 | 10.2 | 14.7 | 19.6 | 24.4 | 3.2 | 4.0 | 5.1 | 6.0 | 7.1 | 8.5 |
| 41 | 21 | 3.2 | 6.0 | 8.9 | 12.9 | 17.1 | 22.2 | 3.1 | 4.2 | 5.1 | 6.0 | 7.5 | 8.3 |
| 42 | 22 | 2.7 | 6.1 | 8.7 | 11.7 | 15.6 | 19.6 | 2.8 | 4.1 | 5.2 | 5.7 | 7.1 | 8.7 |
| 43 | 23 | 3.4 | 7.0 | 9.0 | 12.8 | 16.6 | 22.5 | 3.4 | 4.4 | 5.3 | 6.0 | 7.1 | 8.5 |
| 44 | 24 | 3.0 | 5.5 | 8.1 | 11.3 | 14.7 | 17.8 | 2.8 | 4.4 | 5.0 | 6.2 | 7.3 | 9.0 |
| 45 | 25 | 2.8 | 5.6 | 8.0 | 11.5 | 14.9 | 16.7 | 3.2 | 4.2 | 5.0 | 5.9 | 7.0 | 8.3 |
| | | | | (Comparison tests) | | | | | | | | | |
| 46 | 26 | 3.7 | 11.2 | 18.9 | 27.4 | 37.8 | 52.4 | 3.0 | 3.9 | 5.3 | 6.3 | 7.7 | 9.3 |
| 48 | 28 | 2.8 | 5.8 | 8.9 | 12.6 | 17.6 | 20.4 | 3.0 | 3.8 | 4.4 | 5.3 | 6.2 | 7.2 |

*Test pieces with 0.1% by weight of stabilizer and 0.1% by weight of calcium stearate
**Test pieces in addition contain 0.1% by weight of bis-(octadecyl) thiodipropionic acid ester and 0.1% by weight of tris-(2,4-di-tert-butylphenyl) phosphite

EXAMPLES 50 and 51

(not according to the invention)

According to the procedure described in Example 1, 1,3,5-tribromo-2,4,6-tris-(bromomethyl) benzene (Example 50) or 1,3,5-trimethyl-2,4,6-tris(bromomethyl) benzene (Example 51) are convereted to the corresponding tris-((2-hydroxyethyl-thiomethyl) benzene compounds. The constitution of the obtained triols was verified by $^1$H NMR spectroscopy. The compounds have melting points of 161.5° C. (Example 50) or 163° C.(Example 51).

EXAMPLES 52 and 53

According to the data of Example 2, the triols, produced according to Example 50 or 51, are transesterified by catalysis with titanium tetrabutylate in 14 to 21 hours with 3-(3,5-di-tert-butyl-4-hydroxyphenyl) propionic acid methyl ester. The esters obtained showed melting points of 53° to 55° C. (Example 52) or 99° to 100° C. (Example 53). Their constitution is verified by $^1$H NMR spectra.

Resonance lines in ppm/classification analogously to the structure formula of Table I***.

1: 700 (6) 2: 5.06 (3) 3: 429 (6) 4+5: 2.89 (12)
6: 2.64 (6) 7: 1.43 (54) 9: 4.32 (6) (Example 52)
1: 6.99 (6) 2: 5.08 (3) 3: 4.31 (6) 4: 2.79 (6) 5: 2.89 (6)
6: 2.63 (6) 7:1.43 (54) 9: 3.84 (6) 11; 2.46 (9)

The preceding Examples can be repeated with similar success by substituting the generically or specifically described reactants and/or operating conditions of this invention for those used in the preceding Examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An ester of a 3-tert-butyl or 3-tert-butyl-5-alkyl-4-hydroxyphenyl-(alkane) carboxylic acid of formula I

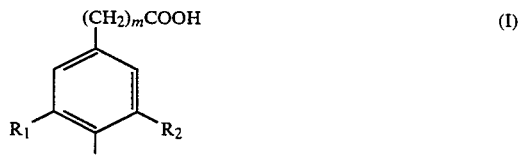

wherein
$R_1$ is $-C(CH_3)_3$
$R_2$ is H or $C_1$ to $C_4$ alkyl,
m is an integer from 0 to 4 inclusive, with an oxethylate of a polythiol aromatic of formulae II or III having 2 to 6 thiol groups

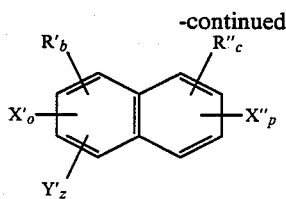

or with an oxethylate of a dithiolcycloalkane of formula IV, which contains a maximum of 6 alkylene oxide units,

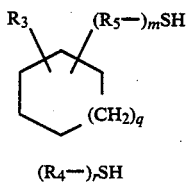

wherein
X is $(CH_2)_m SH$
X' is $(CH_2)_r SH$
X" is $(CH_2)_s SH$, wherein m, r and s represents 0 or 1,
R, R', R" being identical or different are each H, alkyl, halogen or hydroxyl,
$R_3$ is H, $C_1$ to $C_4$ alkyl,
$R_4$, $R_5$ being identical or different are each $C_2$ to $C_4$ alkylene,
q=0 to 7,

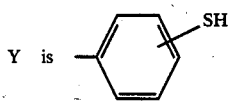

n=2 to 6, inclusive, for z or z'=0,
n=1 to 5, inclusive, for z or z'≠0,
o+p=n
$0 \leqq a$, $z \leqq a+z \leqq 6-n$ (in formula II)
$0 \leqq b, c, z' \leqq 4 \leqq 8-n$ (in formula III).

2. An ester according to claim 1, of 3-(3,5-di-tert-butyl-4-hydroxyphenyl) propionic acid of formula Ia

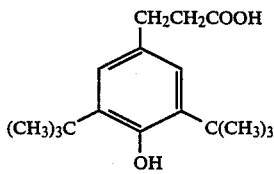

3. An ester according to claim 1, with an oxethylate of a polythiol aromatic of formula II having 2 to 6 thiol groups.

4. An ester according to claim 2, with an oxethylate of polythiol aromatic of formula II having 2 to 6 thiol groups.

5. An ester according to claim 1, with an oxethylate of the polythiol aromatic of formulae II or III, containing one ethylene oxide unit per thiol group as 2-hydroxyethyl thiol groups.

6. An ester according to claim 2, with an oxethylate of the polythiol aromatic of formulae II or III, containing one ethylene oxide unit per thiol group as 2-hydroxyethyl thio groups.

7. An ester according to claim 4, with an oxethylate of the polythiol aromatic of formulae II or III, containing one ethylene oxide unit per thiol group as 2-hydroxyethyl thio groups.

8. An ester according to claim 1, with a bis(monooxethylate) of 1,4 or 1,2-bis-(thiomethyl) benzene or 1,4-bis-(thiomethyl)-2,3,5,6-tetrabromobenzene or with tris-(monooxethylate) of 1,3,5-tris-(thiomethyl)2,4,6-trichlorobenzene or with tetra-(monooxethylates) of 1,4-dichloro-2,3,5,6-tetra-(thiomethyl) benzene or 1,4-dibromo-2,3,5,6-tetra-(thiomethyl) benzene or with penta-(monooxethylate) of penta-(thiomethyl) toluene or with hexa-(monooxethylate) of hexakis-(2-hydroxyethylthiomethyl) benzene or with bis-(monooxethylate) of 2,9-paramenthane dithiol).

9. An ester according to claim 2, with a bis(monooxethylate) of 1,4 or 1,2-bis-(thiomethyl) benzene or 1,4-bis-(thiomethyl)-2,3,5,6-tetrabromobenzene or with tris-(monooxethylate) of 1,3,5-tris-(thiomethyl)2,4,6-trichlorobenzene or with tetra-(monooxethylates) of 1,4-dichloro-2,3,5,6-tetra-(thiomethyl) benzene or 1,4-dibromo-2,3,5,6-tetra-(thiomethyl) benzene or with penta-(monooxethylate) of penta-(thiomethyl) toluene or with hexa-(monooxethylate) of hexakis-(2-hydroxyethylthiomethyl) benzene or with bis-(monooxethylate) of 2,9 - paramenthane dithiol).

10. A stabilized polyolefin comprising a stabilizing amount of an ester according to claim 1.

11. A stabilized polyolefin comprising a stabilizing amount of an ester according to claim 2.

12. A stabilized polyolefin comprising a stabilizing amount of an ester according to claim 3.

13. A stabilized polyolefin comprising a stabilizing amount of an ester according to claim 5.

14. A stabilized polyolefin comprising a stabilizing amount of an ester according to claim 8.

15. A stabilized polyolefin comprising a stabilizing amount of an ester according to claim 9.

16. A stabilized polyolefin according to claim 10, wherein the polyolefin is polyethylene or polypropylene.

17. A stabilized polyolefin according to claim 13, wherein the polyolefin is polyethylene or polypropylene.

18. A stabilized polyolefin comprising a stabilizing amount of an ester according to claim 15.

19. A process of stabilizing a polyolefin by incorporating a stabilizer in said polymer, the improvement wherein the stabilizer is an ester of claim 1.

20. A process according to claim 19, wherein the polymer is polyethylene or polypropylene.

21. A process of stabilizing a polyolefin by incorporating a stabilizer in said polymer, the improvement wherein the stabilizer is as ester of claim 8.

22. A process of stabilizing a polyolefin by incorporating a stabilizer in said polymer, the improvement wherein the stabilizer is an ester of claim 9.

23. An ester according to claim 1, being tris-(3-(3,5-di-tert-butyl-4-hydroxyphenyl) propionic acid ester of 1,3,5-tris-(2'hydroxyethylthiomethyl)-2,4,6,-trichlorobenzene.

24. An ester according to claim 1, with a 1,4-bis-(2'hydroxyethythiomethyl)benzene; 1,2,-bis-2'hydroxyethylthiomethyl)benzene; 1,4-bis-(2'hydroxyethylthiomethyl) 2,3,5,6-tetrabromobenzene; 1,3,5-tris-(2'hydroxyethyl-thiomethyl)-2,4,6-trichlorobenzene; 1,2,4,5-tetra-(2'-hydroxyethyl-thiomethyl)3,6-dichlorobenzene; 1,2,4,5-tetra-(2-hydroxyethyl-thiomethy)-3,6-dibromobenzene; penta-(2'-hydroxyethylthiomethyl) methyl benzene; hexa-(2-hydroxyethylthiomethyl) benzene; bis-2,9-(2'-hydroxyethylthio)para-menthane; or 1,4-dihydroxy-2,3,5,6-tetra-(2'hydroxyethyl-thio) benzene.

* * * * *